(12) United States Patent
Bobbert

(10) Patent No.: US 8,883,074 B2
(45) Date of Patent: Nov. 11, 2014

(54) METHOD FOR BROAD SPECTRUM, LOW RESIDUE DISINFECTION WITH A SMALL DROPLET HYDROGEN PEROXIDE-BASED AEROSOL

(75) Inventor: Ilja Bobbert, Hilversum (NL)

(73) Assignee: Aseptix Research B.V., Loenen Aan de Vecht (NL)

( * ) Notice: Subject to any disclaimer, the term of this patent is extended or adjusted under 35 U.S.C. 154(b) by 497 days.

(21) Appl. No.: 12/673,886

(22) PCT Filed: Sep. 15, 2008

(86) PCT No.: PCT/EP2008/062262
§ 371 (c)(1),
(2), (4) Date: Mar. 26, 2010

(87) PCT Pub. No.: WO2009/037231
PCT Pub. Date: Mar. 26, 2009

(65) Prior Publication Data
US 2010/0189599 A1    Jul. 29, 2010

(30) Foreign Application Priority Data
Sep. 17, 2007    (EP) .................................... 07116566

(51) Int. Cl.
| A61L 2/00 | (2006.01) |
| A61L 2/18 | (2006.01) |
| A01N 59/00 | (2006.01) |
| A61L 2/22 | (2006.01) |
| A61L 9/14 | (2006.01) |
| C11D 3/20 | (2006.01) |
| C11D 3/39 | (2006.01) |
| C11D 3/48 | (2006.01) |

(52) U.S. Cl.
CPC ................. *A61L 2/186* (2013.01); *A01N 59/00* (2013.01); *A61L 2/22* (2013.01); *A61L 9/14* (2013.01); *C11D 3/2079* (2013.01); *C11D 3/3947* (2013.01); *C11D 3/48* (2013.01); *A61L 2202/23* (2013.01); *A61L 2202/25* (2013.01)
USPC ........................................................... 422/28

(58) Field of Classification Search
CPC ............................. A61L 2202/25; A61L 2/186
USPC ........................................................... 422/28
See application file for complete search history.

(56) References Cited

U.S. PATENT DOCUMENTS

| 6,500,465 | B1 | 12/2002 | Ronlan | |
| 2002/0177540 | A1* | 11/2002 | Masotti et al. | 510/278 |
| 2005/0008531 | A1* | 1/2005 | Parkhurst et al. | 422/4 |
| 2005/0019421 | A1 | 1/2005 | Hobbs et al. | |
| 2006/0008379 | A1* | 1/2006 | Mielnik et al. | 422/32 |
| 2007/0289614 | A1* | 12/2007 | McDonnell et al. | 134/42 |

FOREIGN PATENT DOCUMENTS

| BE | 1011452 A6 | 9/1999 |
| EP | 0 948 892 A1 | 10/1999 |
| EP | 0 949 325 A1 | 10/1999 |
| EP | 1 001 012 A1 | 5/2000 |
| WO | WO 2004/045281 A2 | 6/2004 |
| WO | WO 2004/108170 A1 | 12/2004 |
| WO | WO 2007/014437 A1 | 2/2007 |

OTHER PUBLICATIONS

International Search Report mailed on Feb. 5, 2009 in corresponding International Application No. PCT/EP2008/062262.
Written Opinion of the International Searching Authority mailed on Feb. 5, 2009 in corresponding International Application No. PCT/EP2008/062262.

* cited by examiner

*Primary Examiner* — Kevin Joyner
(74) *Attorney, Agent, or Firm* — Oliff PLC

(57) ABSTRACT

The present invention discloses a method for disinfecting a space by applying an aqueous disinfecting composition as a fine aerosol having a droplet size wherein 50% of the droplets have a diameter of at the most 100 μm to a space and leaving the space to air-dry, the aqueous composition comprising: a. hydrogen peroxide in a concentration of 1 to 10% (w/w); b. acyclic carboxylic acid or salt thereof in a concentration of 0.01 to 2% (w/w); c. a humectant in a concentration of 0.05% to 15% (w/w).

23 Claims, No Drawings

METHOD FOR BROAD SPECTRUM, LOW RESIDUE DISINFECTION WITH A SMALL DROPLET HYDROGEN PEROXIDE-BASED AEROSOL

The present invention relates to a method for disinfecting a space by applying a low residue biocidal composition with broad spectrum antimicrobial activity as a fine aerosol.

Resistant bacteria such as Methicillin-Resistant *Staphylococcus aureus* (MRSA) and Vancomycin-Resistant Enterococcus (VRE), Viruses, such as SARS-virus, Influenza A virus H5N1 and Norovirus, and bacterial endospores, such as those of *Bacillus subtilis, Clostridium sporogenes, Clostridium difficile* and *Bacillus anthracis*, pose an important threat to human health. In emergency situations areas, objects or rooms need to be effectively disposed of these rather persistent pathogens without burdening human health. The use of harsh chemicals, human unsafe chemicals or compositions leaving unwanted and difficult to remove residues is highly undesirable.

Killing, inactivating, or otherwise reducing the active population of bacterial spores, fungal spores, and fungi on surfaces (e.g., especially food and healthcare surfaces or instruments and food-contact surfaces, which are typically hard surfaces including metals, glass, composite materials, etc.), and in large rooms also is a difficult problem. In particular, bacterial spores have a unique chemical composition of spore layers that make them more resistant than vegetative bacteria to the antimicrobial effects of chemical and physical agents. A particularly difficult problem relates to microbiocidal treatment of bacterial spore-forming microorganisms of the *Bacillus cereus* group. Microorganisms of the *Bacillus cereus* group include *Bacillus cereus, Bacillus mycoides, Bacillus anthracis*, and *Bacillus thuringiensis*. These microorganisms share many phenotypical properties, have a high level of chromosomal sequence similarity, and are known enterotoxin producers. Like bacterial spores, the unique chemical composition of fungal cells, especially mold spores, makes them more resistant to chemical and physical agents than other microorganisms.

Usually, disinfection comprises a two step process, wherein a substrate to be disinfected is rinsed after application of the disinfectant. However, in some situations, the rinsing step is undesirable or even impossible, for instance in the disinfection of rooms or not easily accessible spaces. Another example is medical instrument sterilization, whereby minimal rinsing after sterilization is desirable.

In such cases where no rinsing is to be applied, it is necessary to use a disinfecting composition that leaves as low residue as possible in the space to be treated.

Low or no residue can only be achieved by using ingredients that do not leave any trace on surfaces after application or by lowering the concentration ranges of the applied ingredients substantially. On the other hand, the active ingredients should provide for sufficient disinfecting activity, implying that the concentration of active ingredients should not be too low and the composition should allow for a sufficient contact time, implying that the composition should not evaporate too quickly.

Some residue-free antimicrobial compositions contain aldehydes, such as glutaraldehyde or formaldehyde, frequently combined with other antimicrobial compounds. For instance, the most widely used method for large area disinfection is fumigation with formaldehyde. Formaldehyde is a suspected carcinogenic and a potent allergen which severely limits its usefulness in structures inhabited by man. In some countries formaldehyde is already banned for airborne disinfection because of their carcinogenic nature. So it is clearly advantageous to decrease or remove aldehydes in disinfection applications.

Other very effective and fast antimicrobials with low residues are based on peracetic acid and derivatives. Besides the pungent odor, and problems with respiratory tracts of users, peracetic acid is highly corrosive and oxidative and therefore not suitable in many situations. The corrosivity causes a major problem when the surface or object is not rinsed afterwards and/or is made of metal.

Several other compounds known in the art to be effective as antimicrobial compounds are completely useless in aerosol or non-wipe applications. Quaternary ammonium compounds, chlorhexidine, biguanides, triclosan, sequestering agents, essential oils, and halogens are leaving substantial, often sticky and difficult to remove, and sometimes even corrosive, residues. Furthermore they are insufficient in their spectrum of efficacy.

Because of the ban in many countries of aldehyde compositions for room and air disinfection, several compositions based on low concentrations of quaternary ammonium compounds have been proposed, mostly in combination with other antimicrobially active substances. However, even low concentrations of quaternary ammonium compounds leave residues which, even after rinsing, are still present and which are highly unwanted, especially in food processing environments. In food processing environments, it is even forbidden in most jurisdictions to use quaternary ammonium compounds without rinsing because of the persistent residues. Again, these compositions do not provide for a sufficiently broad antimicrobial spectrum, especially not against non-enveloped viruses, mycobacteria and bacterial endospores. Disinfection of large spaces with these types of compounds causes substantial drawbacks and severe limitations.

Thus, there is still an unquestionable need for new solutions to treat large spaces effectively and safely.

From a health and environmental point of view, area disinfecting agents based on hydrogen peroxide are much to be preferred. Of the known disinfectants and biocidals, hydrogen peroxide appears to have exceptional potential, because the decomposition products, water and oxygen, are not toxic and not harmful to the environment. Hydrogen peroxide is a no residue disinfectant. Also, it tends to have a broad spectrum biocidal activity. Broad spectrum activity is important for instance in situations where harmful organisms are present but their identity is not known. However, hydrogen peroxide requires long contact times, which is often difficult to achieve in area disinfection whereby the liquid is fogged in small droplets.

Furthermore, hydrogen peroxide is only efficacious against fungi and yeasts with acceptable contact times in relatively high concentrations (8-10% and higher). Bacterial endospores, non-enveloped viruses and mycobacteria are only killed using hydrogen peroxide concentrations that are even higher (generally higher than 10%). At these high concentrations the hydrogen peroxide is highly corrosive and oxidative, negating the positive aspects compared to currently used biocides.

U.S. Pat. No. 6,500,465 discloses the use of a residue free composition comprising hydrogen peroxide, t-butyl hydroperoxide and a water compatible glycol or glycol ether, such as propylene glycol. Hydrogen peroxide and t-butyl hydroperoxide are exemplified in a total concentration of 10, 14% and 17% (w/w). This concentration is considered highly corrosive to materials and skin and highly oxidative.

EP 0 948 892 discloses compositions comprising hydrogen peroxide, a poly(alkylene glycol)alkyl ether and an antimicrobial essential oil. Exemplified compositions further comprise salicylic acid and benzylalcohol as a solvent. The compositions may be packaged in manually operated spray dispensing containers. No mentioning is made of the droplet size of the sprayed composition, nor is the mycobactericidal or sporicidal activity of the compositions mentioned. No rinsing after applying these compositions is only feasible after dilution of the compositions. However, dilution produces a too low hydrogen peroxide concentration for broad spectrum antimicrobial activity. Essential oils are known for leaving a substantial and difficult to remove residue.

EP 0 949 325 discloses a liquid composition suitable for cleaning and sanitizing carpets, comprising a peroxygen bleach, said composition being packaged in a container adapted to deliver the composition onto the carpet in the form of a spray of droplets having a particle size distribution with a mean diameter D(v,0.9) of less than 1500 µm, preferably between 350 and 10 µm.

WO 2007/014437 discloses a method for disinfecting a volume or surfaces bounding a volume comprising ultrasonic nebulization of aqueous hydrogen peroxide, to form a nebulant. The nebulant is subjected to energy of a kind and for a duration sufficient to vaporize the solvent (water) in preference to the sterilizing agent (hydrogen peroxide), to increase the concentration of the sterilizing agent in the nebulant particles.

The objective of the present invention is to provide a method for the disinfection of a space using a biocidal composition that can be applied at ambient conditions as a fine aerosol, in particular as a fog or dry mist, having superior disinfecting strength with respect to microbes and spores thereof adhered to inanimate surfaces, such as walls of a room or objects placed in a room, as well as with respect to airborne microbes and microbial spores.

The objective of the present invention is also to provide a method employing a composition that is to be applied as a penetrating and durable, fine aerosol which does not leave substantial residue and does not require rinsing afterwards.

The objective of the present invention is also to provide a safe and effective method of sanitizing surfaces and ambient air by killing, or reducing or retarding the growth, of pathogenic microorganisms and molds without the use of substances that are toxic to humans and without leaving any permanent residue.

The objective of the present invention is also to provide a method for inactivating viruses, mycobacteria and preferably bacterial endospores. The method should be suitable for emergency decontamination of buildings and spaces infected with hazardous microbes or spores thereof or in the case of a bioterror attack.

Thus, there is provided a method for disinfecting a space by applying an aqueous disinfecting composition as a fine aerosol to the space and leaving space to air-dry, the aqueous composition comprising:
  a. hydrogen peroxide in a concentration of 1 to 10% (w/w);
  b. a cyclic carboxylic acid or salt thereof in a concentration of 0.01 to 2% (w/w);
  c. a humectant in a concentration of 0.05% to 15% (w/w).

The aqueous composition further preferably comprises a level of residue-producing substances of at the most 2% (w/w), more preferably of at the most 1% (w/w), most preferably of at the most 0.5% (w/w).

A space to be disinfected as described herein may be any space comprising any surface and/or object contained therein. A space to be disinfected may be a room or chamber, for example, a shipping container, a hospital ward, an aircraft interior, a shopping mall, a subway system, a warehouse, a silo, or other enclosed or semi-enclosed spaces. Exposed surfaces contained in spaces to be disinfected may be exemplified by surfaces of walls or ceilings or partitions defining the space, or surfaces of objects present in the space, such as work surfaces, machinery surfaces, air conditioning ducts, or other surfaces which are interior or can be enclosed or partly enclosed.

Hydrogen peroxide in combination with a cyclic carboxylic acid and a humectant provides for a highly potent biocide when applied as a fine aerosol, such as a fog or a dry mist, in a space. In order to control hydrogen peroxide decomposition, while still generating a fine aerosol, it was surprisingly found that inclusion of a humectant caused a synergistic effect with specifically the other ingredients of the composition, i.e. hydrogen peroxide and the cyclic carboxylic acid, and provided for a substantial antimicrobial reduction in an aerosol application, especially in large rooms and also on vertical objects or underneath surfaces of objects present in the space to be disinfected. Reducing microbial numbers on vertical objects or underneath surfaces is difficult to achieve. It was also surprisingly found during the investigations that a relatively low hydrogen peroxide concentration could be used, while still attaining high antimicrobial reductions, even on vertical objects and underneath surfaces of objects, causing the compositions to be both highly effective in aerosol application as well as low in corrosivity.

The method of the present invention comprises delivering the compositions as described herein as a fine aerosol, which is defined herein as an aerosol with a small droplet size. A small droplet size is a droplet size wherein 50% of the droplets, preferably 70% of the droplets, more preferably 90% of the droplets, has a diameter of at the most 100 µm, preferably at the most 70 µm, more preferably at the most 50 µm, even more preferably at the most 25 µm, most preferably at the most 10 µm. The lower limit of the droplet size may suitably be as low as 1-2 µm.

It was found that such a small droplet size provides for a higher degree of antimicrobial kill. It was also found that with such a small droplet size, without taking the measures as described herein, the hydrogen peroxide is more rapidly decomposing because of the excess of air around the droplets, reacting with the hydrogen peroxide. Consequently, the hydrogen peroxide is not able to reach distant areas in a space as a reactive molecule.

Especially in large rooms, on vertical structures (such as walls), and underneath horizontal structures (such as tabletops), the antimicrobial killing efficiency of a common hydrogen peroxide aerosol is often insufficient. Higher peroxide concentrations, such as proposed in U.S. Pat. No. 6,500,465, provide for a better disinfection result, but also result in a much higher corrosivity of the composition.

It was found that the inclusion of a humectant in the composition advantageously ensures the production of a small droplet size as defined herein while at the same time causing a synergistic effect with the other specific ingredients of the composition, to provide for a substantial antimicrobial reduction in a fine aerosol application. Furthermore it was found that the presence of a cyclic carboxylic acid in the composition provides for a more stable hydrogen peroxide concentration in the air, when providing the composition as a fine aerosol, than compositions which did not contain the cyclic carboxylic acid.

The compositions as used in the methods as described herein advantageously ensure good disinfection results with a hydrogen peroxide concentration in the air of 25 ppm-100 ppm, preferably about 50 ppm-100 ppm, which can be obtained with a relatively short contact time of 10 to 15 minutes. By combining the ingredients in the compositions as used in the methods of the present invention, an optimum in droplet size of the aerosol and stability of ingredients in the air could be attained, to provide high disinfection strength and low residues.

The compositions are applied as a fine aerosol spray as defined herein using a room fogging device. Examples of devices, which can generate such fine aerosols, are thermal foggers, electric foggers, pressurized air foggers, ultrasonic foggers and low energy vaporizers. Examples of thermal foggers are the Patriot range of Curtis Dynafog, and the Pulsfog range of Dr. Stahl. Examples of pressurized air foggers are the ColdFogger by Frans Veugen. Examples of electric foggers are the Fogmax of CITC, Fogmaster series of The Fogmaster Corporation, Nebulo Fogger of Igeba, Fontan Turbostar of Swintec. Examples of ultrasonic foggers are FG 620 and 4-MFG6R02 of Shira, and Ultra-fogger of Frans Veugen. An example of a low energy vaporizer is disclosed in US 2007/0098591. Foggers can come in the form of stand-alone or mounted fogging machines, or carryable foggers or fog sprayers, for example backpacked (such as SP systems Yard Tender or Birchmeier Spraymatic 10B) or handheld (such as Birchmeier Spraymatic 5 P, 5 S or 10 SP or Hudson).

To obtain fine aerosols with a very small droplet size of at the most 50 or 25 or 10 µm, an ultrasonic fogger preferably is used.

The specific compositions to be used in the method as described herein are thus fine-tuned to produce a small droplet size but on the other hand not to lose the droplets by evaporation via a too low surface tension. The compositions to be used are further fine-tuned to have a rather low evaporation rate and a greater wetting capacity. The composition to be used may further be fine-tuned dependent on the fogging device used.

In the method and composition as described herein, the lower limit of the hydrogen peroxide concentration may be 1%, preferably 2%, more preferably 3% (w/w). Hydrogen peroxide is commercially available as an approximately 3-55% solution in water, typically about 35%, which is then diluted by water and other components of the composition to the desired level. Other sources of peroxide which yield peroxide ions in an equivalent molar amount are also contemplated. For example, the aqueous composition may be prepared by including reagents which form peroxide ions on mixing, e.g. of solid peroxide compounds in water.

The invention contemplates the use of a concentrated composition with hydrogen peroxide concentrations up to 50%, which is diluted to a use composition prior to its application. Primarily for reasons of economics, the concentrate would normally be marketed and an end user would dilute the concentrate with water or an aqueous diluent to a use composition having the appropriate hydrogen peroxide concentration.

The cyclic carboxylic acid is preferably chosen from furoic acid, salicylic acid and/or benzoic acid and is present in a concentration from 0.01% to 2% (w/w), preferably from 0.05% to 1% (w/w), more preferably from 0.1% to 0.5% (w/w).

Furthermore, the composition comprises a humectant. In the context of the invention, a humectant is a compound that promotes the retention of moisture and retards evaporation of a composition to which it is added. For the compositions as described herein, the humectant is suitably selected to ensure a small droplet size of the aerosol, as described herein, while providing the aerosol with an increased wetting capacity and a reduced evaporation rate. By a lowering of the evaporation of the aerosol droplets, the contact time for biocidal activity is prolonged.

Suitable humectants include polyhydroxy compounds, such as tri- or dihydroxycompounds like glycerol, propylene glycol, ethylene glycol, dipropylene glycol, butylene glycol, hexylene glycol, and/or aromatic alcohols, such as benzylalcohol, benzyloxyethanol, phenoxyethanol, phenoxypropanol, phenoxyisopropanol, phenylbutanol, methylisopropylphenol, o-phenylphenol, 1-phenoxy-2-propanol, 2-phenoxy-1-propanol, 3-phenoxy-1-propanol, 1-phenoxy-2-butanol, 2-phenoxy-1-butanol, 1-phenylethylalkohol, 2-phenylethylalkohol, 3-phenyl-1-propanol, alpha-4-dimethylbenzylalkohol, and mixtures thereof. The humectant is preferably present in a concentration of 0.1% to 15 (w/w), more preferably 0.2% to 10% (w/w).

Preferred humectants are glycerol, propylene glycol, butylene glycol, phenoxyethanol, phenoxypropanol and/or benzyl alcohol. If a non-volatile or less volatile humectant is chosen, such as glycerol, the concentration may be in the lower ranges up to 2%, to provide a suitably low residue level upon application of the aerosol and subsequent drying.

In order to produce a fine aerosol containing droplets that are sufficiently small, as described herein, the composition may optionally be supplemented with a volatile C2-C6 aliphatic alcohol. The volatile C2-C6 aliphatic alcohol encompasses aliphatic, straight and/or branched, mono- and/or di-alcohols. Examples of such aliphatic alcohols are ethanol, n-propanol, iso-propanol, n-butanol, sec-butanol, iso-butanol, n-pentanol, n-hexanol and the like, or a combination thereof. In a specifically preferred embodiment, the volatile C2-C6 alcohol is chosen from ethanol, propanol, isopropanol, butanol, n-butanol.

The alcohol, or a combination of alcohols, may be present in a concentration in the range of 0.05% to 15% (w/w), preferably between 0.1% and 10% (w/w).

Certain aromatic alcohols have multiple functions. Such functions encompass, amongst others, the reduction of the aerosol droplet size, thereby enhancing the activity and efficiency of the composition, and the increase of the wetting capacity of the composition. The composition thus can be optimized by the choice of alcohols and the concentration levels thereof. Furthermore, certain aromatic alcohols increase solubility of certain preferred carboxylic acids at lower pH values, so that less residue is obtained by optimizing the composition with as little as possible ingredients.

It was surprisingly found that compositions containing low concentrations of a cyclic carboxylic acid in combination with hydrogen peroxide and further combined with a humectant, applied as an aerosol with a small droplet size as described herein, provide for a broad spectrum disinfectant with reduced contact times. Such aerosol compositions are not only bactericidal, but also fungicidal, mycobactericidal and virucidal, and even sporicidal with acceptable contact times. Such a broad spectrum of antimicrobial activity was previously only possible by using aldehydes or higher concentrations of peracetic acid, or applying very long exposure times. Long exposure times are unpractical in spray or aerosol applications because the composition will evaporate from the surface before reaching the required contact time, which often is required to be up to 30-60 minutes or even several hours, up to 6-24 hours for sporicidal activity.

Throughout this invention, weight percentages (w/w) are based on the total weight of the composition.

The residue level of an aqueous composition may be measured by (1) weighing an inert, clean, flat and non-porous object (e.g. an inert glass plate), (2) applying a known amount of the aqueous composition to the object and allowing it to spread without spilling, (3) leaving the object to air-dry for a time period to allow the liquid to fully evaporate (typically, this time period may be from 30 to 240 minutes), and (4) weighing the object. In one embodiment of the invention, the preferable maximum allowable weight increase may be 2% of the weight of the applied aqueous composition.

The aqueous composition may have a pH between 1 and 12, especially at higher alkaline conditions for situations where prion deactivation is required, but is preferably between 1.5 and 8, more preferably between 2 and 5. The pH of the composition may be adjusted by an appropriate amount of acid or base.

The aqueous composition may further contain optional compounds, such as hydrogen peroxide stabilizers, surfactants, anti-corrosive agents. These compounds are commonly known in the art for incorporation in hydrogen peroxide compositions.

The stabilizer is present in a sufficient amount to maintain the stability of hydrogen peroxide in the composition until its use and to maintain the stability in the presence of soil at a sufficient concentration to allow the hydrogen peroxide to destroy microorganisms. The amount of the stabilizer present is dependent on the type of stabilizer used and whether the composition is to be formed immediately prior to use or to be stored for many weeks or months. Additionally, if tap water rather than deionized water is used in the composition, slightly higher concentrations of stabilizer may be appropriate.

The composition may comprise one or more corrosion inhibitors, especially when used in acidic pH range and higher hydrogen peroxide concentrations. It is often preferable to have one or more corrosion inhibitors in the composition, such that the composition may be applied on a variety of metal substrates. Corrosion inhibitors are present at sufficient concentrations to inhibit corrosion of the medical instruments or other devices during the period of exposure to the composition.

Furthermore the composition contains preferably a surface active agent. Surface active agents which can be used in the composition include any of those constituents known within the art to raise the surface activity of the composition, to increase penetration into crevices of items being treated. Preferred surfactants ensure an increased wetting and penetration capacity of the composition. These preferred surfactants include nonionic surfactants and amphoteric surfactants. Preferred nonionic surfactants are straight-chain or branched C8-C18 fatty alcohol ethoxylates and/or alkylpolyglucosides. Preferred amphoteric surfactants are amine oxides, betaines, hydroxysultaines, alkyl amines, alkyl amides and/or amphoteric imidazoline derivatives.

It is preferred to use an ultrasonic fogger to provide for the smallest droplet size possible, such as at the most 50 or 25 or 10 μm. However, when using an ultrasonic fogger, care should be taken that the composition should not contain a surfactant in a concentration that produces foaming during creation of such a fine aerosol. For instance, foaming surfactants like alkyl sulfates, alkyl sulfosuccinates, alkylethersulfates, ethoxylated alcohols, ethoxylated fatty acids, amine oxides, etc. may only be present in low concentrations of e.g. at the most 0.05% or 0.1% or 0.2% (w/w) or not be present at all.

When incorporating any optional compound in the composition, care should be taken not to exceed the residue level as required for the use composition.

The remainder of the composition suitably may be water.

The compositions and methods as described herein are effective against a wide variety of microorganisms, such as Gram-positive and Gram-negative bacteria, yeast, molds, bacterial spores, viruses, etc. The compositions and methods are effective in killing a wide variety of human pathogens, such as *Salmonella typhimurium, Staphylococcus aureus, Pseudomonas aeruginosa, Mycobacteria, Legionella, Campylobacter jejuni, Listeria monocytogenes*, and *Escherichia coli* 0157:H7. They are very effective for air disinfection, for instance in case of the presence of viruses or bacterial or fungal spores. The composition may be sporicidal and may be effectively used to remove *Bacillus anthracis* (anthrax) spores from the air and/or surfaces. The compositions and methods can kill a wide variety of microorganisms on a food processing surface, a healthcare surface, or in room disinfection purposes, by way of aerosol application.

Preferably, the aqueous composition produces a log 5 reduction in 2 minutes on *Staphylococcus aureus* and a log 5 reduction in 10 minutes on *Aspergillus niger* in a controlled suspension test.

The compositions and method as described herein may also be active against prions. They find application in conjunction with the treatment of spaces that contain surfaces and/or equipment contaminated with prions, such as medical and food surfaces and equipment and medical and surgical instruments. The term "Prion" is used to describe proteinaceous-infectious agents that cause relatively similar brain diseases in humans and/or in animals, which are invariably fatal. Prions are very resistant to deactivation. Unlike microorganisms, prions have no DNA or RNA to destroy or disrupt. Prions, due to their hydrophobic nature, tend to aggregate together in insoluble clumps. Under many conditions that lead to successful sterilization with respect to microorganisms, prions form tighter clumps which protect themselves and underlying prions from the sterilization process. Because of the small droplet size and the wetting capacity of the compositions as described herein and the oxidizing power of hydrogen peroxide, prions may be successfully deactivated.

Compositions aimed at prion deactivation are preferably at a higher pH and may further contain specific surfactants and solvents that enhance protein solubilisation and penetration of the composition into the protein clumps. Preferably specific volatile solvents with high solvency power are used in such composition. Examples of preferred solvents are propyleneglycolethers, such as 1-ethoxy-2-propanol, 1-butoxy-2-propanol, 1-(2-methoxy-2-methylethoxy)-2-propanol, dipropylene glycol methyl ether, 1-(2-butoxy-2-methylethoxy-2-propanol, etc.

In one embodiment, the composition is used as a more-component composition. Examples are one component containing water, hydrogen peroxide, a carboxylic acid and optionally a stabilizer. The second component containing a wetting agent and other volatile ingredients. Furthermore, the two component system may be used against prions. Prion deactivation with hydrogen peroxide occurs at higher pH and with supporting substances. The base component may then be at lower pH (maintain a stable hydrogen peroxide composition), whereby the second component is of higher pH and contains supporting substances and optionally activators.

The present method requires a certain minimum contact time of the composition with the contaminated space to achieve a significant antimicrobial effect. The contact time may vary with type of application, concentration of the use composition, temperature of the use composition, amount of soil that is present, number of microorganisms that are present. In general, the exposure time may be from 5 or 10 to about 60 minutes. In a room disinfection application, the exposure time may be at least 10 minutes, but a treated room may conveniently be left for 12 to 24 hours after exposure to the fine aerosol.

The method of the present invention is particularly suitable for disinfection of large spaces. By applying a small droplet size aerosol, preferably by using an ultrasonic fogger to provide a so-called "dry mist", the method provides for a substantially improved disinfection result. The method as described herein provides a fine balance between droplet size, evaporation rate and degradation versus stability of the hydrogen peroxide, a low residue and still a broad spectrum of antimicrobial efficacy. Using the compositions presented it was found that a surprisingly high disinfection capacity with a very low residue and a simple and relatively short operating procedure can be effectively combined.

EXAMPLES

Suspension Testing

Biocidal activity of the exemplified compositions was tested using a controlled bactericidal suspension test conform European Norm for chemical disinfectants and antiseptics EN 1276 (EN 1276: Quantitative suspension test for the evaluation of bactericidal activity of chemical disinfectants and antiseptics used in food, industrial, domestic, and institutional areas: test method and requirements). One ml of a test suspension containing about $10^8$ cfu of the test microorganism per ml is added to 8 ml of the composition to be tested, and 1 ml milli-Q water is added. After a contact time of a few minutes, as indicated below, the amount of viable bacteria was determined. The EN 1276 norm prescribes a log 5 reduction in viable count after a contact time of 5 minutes.

Similarly, the fungicidal activity was tested in a EN 1650 suspension test, the mycobactericidal activity in a EN 14348 suspension test and the sporicidal activity in a EN 13704 suspension test.

In some experiments, a protein load was added to the suspension according to the EN 1276 or EN 1650 procedure to simulate unclean practical conditions. To provide for a clean condition 0.3% Bovine Albumin was added and for a dirty condition 3% Bovine Albumin.

In the specific application of a composition by spraying or fogging as a fine aerosol without wiping or rinsing afterwards, it appeared that the most resistant micro-organisms were the bacterium *Staphylococcus aureus* and the fungus *Aspergillus niger*. It is suspected that in this type of application *Staphylococcus aureus* is a particularly resistant organism because of its catalase production, effectively degrading hydrogen peroxide. Practical tests performed by applicant proved that suspension tests performed on *Staphylococcus aureus* (ATCC 6538) and *Aspergillus niger* (ATCC 16404), using relatively short contact times, produce an effective model to predict the antimicrobial kill efficacy against a complete spectrum of micro-organisms (bacteria, viruses, fungi, mycobacteria en bacterial endospores) in a fine aerosol application. A series of suspension tests in dirty conditions (according European norms EN 1276 and EN 1650, respectively) were performed to evidence the efficacy of various compositions (see Table below) on these two microorganisms.

All compositions have a pH between 2.5 and 3.5.

| | | Log Reductions |
|---|---|---|
| | *Staphylococcus Aureus* ATCC 6538 | 2 min |
| II | 5% H2O2 + 0.5% Furoic Acid | 2.3 |
| III | 3% H2O2 + 0.3% Furoic Acid | <2.0 |
| IV | 2% H2O2 + 2.5% Benzyl Alcohol | 3.5 |
| V | 3% H2O2 + 2% Phenoxyethanol | >6.5 |
| IX | 5% H2O2 + 1% Phenoxyethanol + 0.3% Salicylic Acid + 2% propylene glycol | >6.5 |
| X | 5% H2O2 + 1% Phenoxyethanol + 0.3% Benzoic Acid + 2% propylene glycol | >6.5 |
| XI | 5% H2O2 + 1% Phenoxyethanol + 0.3% Lactic Acid + 2% propylene glycol | >6.5 |
| XII | 5% H2O2 + 2% Phenoxyethanol + 0.3% Furoic Acid | >6.5 |
| XIII | 5% H2O2 + 5% Propanol + 0.3% Furoic Acid + 5% propylene glycol | >6.5 |
| XIV | 5% H2O2 + 10% Isopropanol + 0.4% Salicylic Acid + 1% butylene glycol | >6.5 |
| XV | 5% H2O2 + 10% Ethanol + 0.5% Furoic Acid + 0.5% glycerol | >6.5 |
| | *Aspergillus Niger* ATCC 16404 | 15 min |
| I | 5% H2O2 + 2.5% Benzyl alcohol | 2.2 |
| II | 5% H2O2 + 0.5% Furoic Acid | >5.5 |
| III | 3% H2O2 + 0.3% Furoic Acid | >5.4 |
| | | 10 min |
| IV | 2% H2O2 + 2.5% Benzyl alcohol | <1 |
| V | 3% H2O2 + 2% Phenoxyethanol | <1 |
| IX | 5% H2O2 + 1% Phenoxyethanol + 0.3% Salicylic Acid + 2% propylene glycol | >5.2 |
| X | 5% H2O2 + 1% Phenoxyethanol + 0.3% Benzoic Acid + 2% propylene glycol | >5.2 |
| XI | 5% H2O2 + 1% Phenoxyethanol + 0.3% Lactic Acid + 2% propylene glycol | <1 |
| XII | 5% H2O2 + 2% Phenoxyethanol + 0.3% Furoic Acid | >5.2 |
| XIII | 5% H2O2 + 5% Propanol + 0.3% Furoic Acid + 5% propylene glycol | >5.2 |
| XIV | 5% H2O2 + 10% Isopropanol + 0.4% Salicylic Acid + 1% butylene glycol | >5.2 |
| XV | 5% H2O2 + 10% Ethanol + 0.5% Furoic Acid + 0.5% glycerol | >5.2 |
| | *Bacillus subtilis* spores | 90 min |
| XVI | 7% H2O2 + 0.3% Furoic Acid + 2% Propylene Glycol + 5% Propanol | 3.8 |

It appears that compositions containing $H_2O_2$, a cyclic carboxylic acid and a humectant (benzyl alcohol, phenoxyethanol, propylene glycol, and/or butylene glycol, see compositions IX, X, XII, XIII, XIV, XV) displayed a high biocidal activity on both *S. aureus* as well as *A. niger*, as compared to the low biocidal activity of compositions lacking one of these components (see compositions I, II, III, IV, V and XI). In addition, a good sporicidal activity was obtained (composition XVI).

Aerosol Application Using a <100 μm Aerosol

An electric room fogging device manufactured by Fogmaster Corporation was used, producing an aerosol having droplets with a droplet size of about 100 μm. The aerosol was applied in a 12 ml/m³ quantity. A room of 40 m³ was fogged for 20 minutes. After fogging the room was left for 3 hours to let the hydrogen peroxide concentration decrease to a safe level to enter the room.

At 2-3 meters distance of the room fogging device several Petri dishes with dried inoculum of $10^6$ to $10^8$ microorganisms per milliliter were placed. After application, the room was left unventilated for 3 hours, after which the reduction in antimicrobial count was measured. This was done by rinsing off the microbial residue from the petri dish, suspending this in a known volume of liquid medium (physiological salt or agar), plating out the suspension on a petri dish containing a growth medium and incubating the plate for the appropriate time period (depending on the micro-organism. After this, the plates were counted and the survival calculated.

Several compositions (see Table below) were tested in this aerosol application against *Pseudomonas aeruginosa, E. coli, Bacillus subtilis, Clostridium sporogenes, Staphylococcus aureus, Enterococcus hirae, Candida albicans*, and *Aspergillus niger*.

A 5% H2O2+2.5% Benzyl alcohol+0.1% Furoic Acid
B 8% H2O2+6% Propylene Glycol+0.3% Furoic Acid
C 6% H2O2+2% Phenoxyethanol+0.2% Furoic Acid+5% Propanol
D 5% H2O2+2% Phenoxyethanol+0.2% Furoic Acid+0.2% C12 amine oxide
E 4% H2O2+2% Phenoxyethanol+0.2% Benzoic Acid+5% Propylene Glycol
F 7% H2O2+0.2% Salicylic Acid+5% Propylene Glycol+5% Isopropanol+0.05% C10 fatty alcohol
G 6% H2O2+0.3% Furoic Acid Composition A (with a 5 hour contact time after application), provided for at least a log 5 reduction in *Pseudomonas aeruginosa, E. coli, Bacillus subtilis, Staphylococcus aureus*. However, *Aspergillus niger* was not reduced sufficiently.

Composition B also provided a log 4 reduction of *Aspergillus niger*.

Composition C provided a reduction greater than log 6 in all tested organisms, ranging from bacteria to fungi and bacterial endospores.

Composition D provided a greater than log 6 reduction in all tested organisms.

Composition E provided a reduction greater than log 6 in all tested organisms, ranging from bacteria to fungi and bacterial endospores.

Composition F provided a greater than log 5 reduction in all tested organisms.

Composition G, which is not according this invention, provided an insufficient reduction on *Aspergillus niger, Staphylococcus aureus* and *Bacillus subtilis*.

Aerosol Application Using a <10 μm Aerosol

An ultrasonic room fogging device manufactured by Frans Veugen BV was used, producing an aerosol having droplets with a droplet size of around 8 μm (in a Gaussian distribution with >90% smaller than 10 μm). The room had a volume of 40 m³. The aerosol was applied in a 5 ml/m³ quantity for a period of 15 minutes. After the 15 minutes, the room was fully misted and the degree of density of the mist is indicated below.

In the room several mirror plates of 10×10 cm were placed for evaluation of the residue caused by the composition. After 10 fogging cycles the residue was visually observed by evaluating the residue on the mirror plates with and without touching the plate.

Furthermore the concentration hydrogen peroxide was measured with a Dräger hydrogen peroxide measurement device (Dräger Chip Measurement System) to follow the concentration of hydrogen peroxide in the air during fogging and after the fogging equipment was switched off. Practical tests have indicated that a concentration in the air of at least 25 ppm is required for good disinfection results. In this case, the concentration was brought up to around 50-60 ppm and stayed at around 50 ppm for at least 10 minutes. This aspect is mentioned in the table under "Concentration Stability".

After fogging the room was left for 2 hours to let the hydrogen peroxide concentration decrease to a safe level to enter the room.

At 1 and 2 meters distance of the room fogging device several Petri dishes with dried inoculum of $10^6$ to $10^8$ microorganisms per milliliter were placed. After application, the room was left unventilated for 2 hours, after which the reduction in antimicrobial count was measured. This was done by rinsing off the microbial residue from the petri dish, suspending this in a known volume of liquid medium (physiological salt or agar), plating out the suspension on a petri dish containing a growth medium and incubating the plate for the appropriate time period (depending on the micro-organism. After this, the plates were counted and the survival calculated.

Several compositions (see Table below) were tested in this aerosol application against *Staphylococcus aureus*, and spores of *Bacillus cereus* and *Aspergillus niger*.

Composition Overview

A 4% Hydrogen peroxide+1% Monopropylene glycol+0.1% Salicylic acid+5% ethanol
B 5% Hydrogen peroxide+3% Monopropylene glycol+0.2% Furoic acid
C 4% Hydrogen peroxide+0.5% Monopropylene glycol+ 0.2%
Salicylic acid+2% propanol
D 5% Hydrogen peroxide
E 5% Huwa San (a commercially available product of hydrogen peroxide stabilized with colloidal silver. Manufacturer Roam Chemie NV of Belgium)
F 5% Sanosil (a commercially available product of hydrogen peroxide stabilized with silver nitrate. Manufacturer Sanosil Ltd of Switzerland)

| Composition | Density mist | Concentration stability (ppm) | Residue after fogging | Log Reductions | | |
|---|---|---|---|---|---|---|
| | | | | S. aureus | B. cereus spores | A. niger spores |
| A | Very High | High | None | >log 6 | >log 6 | >log 6 |
| B | Very High | High | None | >log 6 | >log 6 | >log 6 |
| C | Very High | High | Virtually none | log 5 | >log 6 | >log 6 |
| D | Low | Low (drops fast) | None | TNC | TNC | TNC |

-continued

| Composition | Density mist | Concentration stability (ppm) | Residue after fogging | Log Reductions | | |
|---|---|---|---|---|---|---|
| | | | | S. aureus | B. cereus spores | A. niger spores |
| E | Medium | Medium | Virtually none | log 4 | log 3 | TNC |
| F | Low | Medium | Bluegray layer | log 3 | TNC | TNC |

TNC = too numerous to count (plate overgrown, no reduction measurable)

It is evidenced that compositions that do not contain a cyclic carboxylic acid and a humectant do not produce a high density mist and display a low concentration stability and a low antimicrobial kill.

The compositions as used herein provide for an increased stability of the hydrogen peroxide concentration in the air and are able to produce relatively high concentrations (50-60 ppm) in the air in a short time frame (minutes). This greatly improves the disinfection results.

The invention claimed is:

1. A method for disinfecting a space, the space being a room or a chamber, by applying an aqueous disinfecting composition as a fine aerosol having a droplet size wherein 50% of the droplets have a diameter of at the most 100 μm to the space and leaving the space to air-dry, the aqueous composition comprising:
  a. hydrogen peroxide in a concentration of 1 to 10% (w/w);
  b. a cyclic carboxylic acid or salt thereof in a concentration of 0.01 to 2% (w/w); and
  c. a humectant in a concentration of 0.05% to 15% (w/w), the aqueous composition having a pH of 1 to 6, wherein the applying of the aqueous disinfecting composition produces at least a log 5 reduction in 2 minutes on *Staphylococcus aureus* in a controlled suspension test in accordance with EN 1276 and at least a log 5 reduction in 10 minutes on *Aspergillus niger* in a controlled suspension test in accordance with EN 1650.

2. The method according to claim 1, wherein the aqueous composition comprises a level of residue-producing substances of less than 2% (w/w).

3. The method according to claim 1, wherein 70% of the droplets have a diameter of at the most 100 μm.

4. The method according to claim 1, wherein 50% of the droplets have a diameter of at the most 70 μm.

5. The method according to claim 1, wherein the cyclic carboxylic acid is chosen from furoic acid, salicylic acid and/or benzoic acid.

6. The method according to claim 1, wherein the humectant is chosen from a polyhydroxy compound and/or an aromatic alcohol.

7. The method according to claim 6, wherein the polyhydroxy compound is chosen from propylene glycol, dipropylene glycol, ethylene glycol, butylene glycol and/or glycerol.

8. The method according to claim 6, wherein the aromatic alcohol is chosen from benzyl alcohol, phenoxypropanol and/or phenoxyethanol.

9. The method according to claim 1, wherein the composition further comprises a volatile C2-C6 aliphatic alcohol.

10. The method according claim 9, wherein the volatile C2-C6 aliphatic alcohol is chosen from at least one of ethanol, isopropanol, propanol, n-butanol and/or n-pentanol.

11. The method according to claim 1, wherein the aqueous composition further comprises a nonionic and/or amphoteric surfactant.

12. The method according to claim 11, wherein the nonionic surfactant is chosen from the group of C8-C18 fatty alcohol alkoxylates and/or alkylpolyglucosides.

13. The method according to claim 11, wherein the amphoteric surfactant is chosen from the group of amine oxides, betaines, hydroxysultaines, alkyl amines, alkyl amides and amphoteric imidazoline derivatives.

14. The method according to claim 1, wherein the composition does not contain a surfactant that produces foaming when creating a fine aerosol with an ultrasonic fogger.

15. The method according to claim 1, wherein the disinfecting comprises the inactivation of prions.

16. The method according to claim 1, wherein the aerosol is produced by an automatic room fogging device.

17. The method according to claim 1, wherein 50% of the droplets have a diameter of at the most 50 μm.

18. The method according to claim 1, wherein 50% of the droplets have a diameter of at the most 25 μm.

19. The method according to claim 1, wherein 50% of the droplets have a diameter of at the most 10 μm.

20. The method according to claim 1, wherein the fine aerosol provides a hydrogen peroxide concentration in the air of 25 ppm-100 ppm.

21. The method according to claim 1, wherein the applying the aqueous disinfecting composition also disinfects exposed surfaces within the space.

22. The method according to claim 1, wherein the cyclic carboxylic acid is one or more of furoic acid, salicylic acid and benzoic acid, and the humectant is one or more of propylene glycol, dipropylene glycol, ethylene glycol, butylene glycol, glycerol, benzyl alcohol, phenoxypropanol and phenoxyethanol.

23. The method according to claim 1, wherein the aqueous composition has a pH of 1 to 5.

* * * * *